United States Patent
Heinemann et al.

(12)
(10) Patent No.: US 6,348,471 B1
(45) Date of Patent: *Feb. 19, 2002

(54) PYRIMIDYL OXYPHENYLACETIC ACID DERIVATIVES

(75) Inventors: Ulrich Heinemann, Leichlingen; Herbert Gayer, Monheim; Peter Gerdes, Aachen; Ralf Tiemann, Leverkusen; Astrid Mauler-Machnik, Leichlingen; Stefan Dutzmann, Langenfeld; Klaus Stenzel, Düsseldorf, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,797
(22) PCT Filed: Jul. 9, 1998
(86) PCT No.: PCT/EP99/04258
§ 371 Date: Jan. 12, 2000
§ 102(e) Date: Jan. 12, 2000
(87) PCT Pub. No.: WO99/05122
PCT Pub. Date: Feb. 4, 1999

(30) Foreign Application Priority Data

Jul. 22, 1997 (DE) .......................... 197 31 322

(51) Int. Cl.$^7$ ........................ C07D 239/52; A01N 43/54
(52) U.S. Cl. ....................................... 514/274; 544/309
(58) Field of Search ........................... 544/309; 514/274

(56) References Cited

U.S. PATENT DOCUMENTS

| 5,185,342 A |   | 2/1993  | Hayase et al. | 514/274 |
| 5,206,245 A | * | 4/1993  | Clough        | 514/269 |
| 5,371,222 A |   | 12/1994 | Hayase et al. | 544/316 |
| 5,371,223 A |   | 12/1994 | Hayase et al. | 544/316 |
| 5,401,877 A |   | 3/1995  | Hayase et al. | 564/147 |
| 5,548,078 A |   | 8/1996  | Hayase et al. | 544/298 |

FOREIGN PATENT DOCUMENTS

| GB | 2249092  |   | 4/1992 |
| WO | 95/24396 | * | 9/1995 |

OTHER PUBLICATIONS

Chem. Ber. 101, pp. 2132–2142 (month unavailable) 1968, Eckard Wittenberg, Synthese der anomeren 2'–Desoxy–D–ribopyranosyl–uracile.

* cited by examiner

Primary Examiner—Richard L. Raymond
Assistant Examiner—Hong Liu
(74) Attorney, Agent, or Firm—Joseph C. Gil

(57) ABSTRACT

The invention relates to novel pyrimidyloxyphenylacetic acid derivatives, to a plurality of processes for their preparation and to their use to fungicides, and also to novel intermediates and to a process for their preparation.

9 Claims, No Drawings

PYRIMIDYL OXYPHENYLACETIC ACID DERIVATIVES

The invention relates to novel pyrimidyloxyphenylacetic acid derivatives, to a plurality of processes for their preparation and to their use as fungicides, and also to novel intermediates and to a process for their preparation.

It is already known that certain pyrimidyloxyphenylacetic acid derivatives, such as, for example, methyl 2-(methoxyimino)-2-[[4-(2,2,2-trifluoroethoxy)-2-pyrimidyl]oxy]-phenylacetate, 2-(methoxyimino)-N-methyl-2-[[4-(2,2,2-trifluoro-ethoxy)-2-pyrimidyl]oxy]-phenylacetamide, methyl 2-(methoxyimino)-2-[[4-(2,2,2-trifluoro-1-methylethoxy)-2-pyrimidyl]oxy]-phenylacetate and 2-(methoxyimino)-N-methyl-2-[[4-(2,2,2-trifluoro-1-methylethoxy)-2-pyrimidyl]oxy]-phenylacefamide, which have a constitution similar to those described below, have fungicidal properties (compare, for example, WO 95-24396 or EP 398692). However, the fungicidal activity of these compounds is unsatisfactory, in particular at low application rates.

This invention, accordingly, provides the novel pyrimidyloxyphenylacetic acid derivatives of the general formula (I)

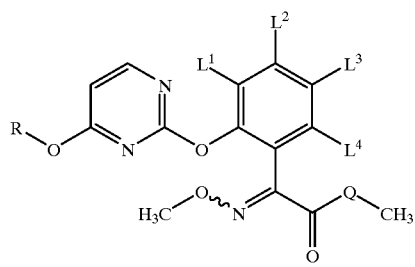

in which
R represents in each case optionally substituted alkyl, alkenyl, alkinyl, cycloalkyl or cycloalkenyl, except for 2,2,2-trifluoroethyl and 1-methyl-2,2,2-trifluoroethyl,
Q represents oxygen or —NH—, and
$L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or alkinyl, are in each case straight-chain or branched, including combination with heteroatoms, such as in alkoxy, alkylthio or alkylamino.

Halogen generally represents fluorine, chlorine, bromine or iodine, preferably fluorine, chlorine or bromine, in particular fluorine or chlorine.

Cycloalkyl represents saturated, carbocyclic, cyclic compounds which optionally form a polycyclic ring system with other carbocyclic, fused-on or bridged rings.

Cycloalkenyl represents carbocyclic, cyclic compounds which contain at least one double bond and which optionally form a polycyclic ring system with other carbocyclic, fused-on or bridged rings.

Furthermore, it has been found that the novel pyrimidyloxyphenylacetic acid derivatives of the general formula (I) are obtained when (process a) 4-halogeno-2-phenoxypyrimidines of the general formula (II)

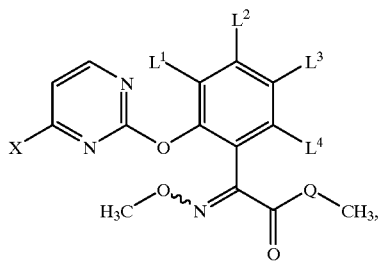

in which
Q, $L^1$, $L^2$, $L^3$ and $L^4$ are as defined above and
X represents halogen
are reacted with an alcohol of the general formula

R—O—H (III), in which
R is as defined above,
if appropriate in the presence of a diluent and if appropriate in the presence of an acid acceptor,
or when (process b) alkylsulphonylpyrimidines of the general formula (IV)

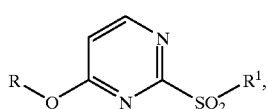

in which
R is as defined above and
$R^1$ represents alkyl or arylalkyl,
are reacted with a 2-(1-hydroxyphenyl-1-methoximino) acetic acid derivative of the general formula

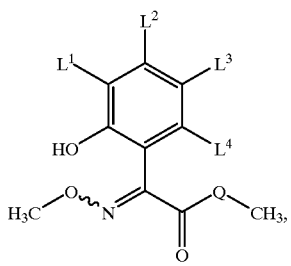

in which
Q, $L^1$, $L^2$, $L^3$ and $L^4$ are as defined above,
if appropriate in the presence of a diluent and if appropriate in the presence of an acid acceptor.

Finally, it has been found that the novel pyrimidyloxyphenylacetic acid derivatives of the general formula (I) have very strong fungicidal activity.

Surprisingly, the compounds according to the invention have better fungicidal activity than methyl 2-(methoxyimino)-2-[[4-(2,2,2-trifluoroethoxy)-2-pyrimidyl]oxy]-phenylacetate, 2-(methoxyimino)-N-methyl-2-[[4-(2,2,2-trifluoroethoxy)-2-pyrimidyl]oxy]-phenylacetamide, methyl 2-(methoxyimino)-2-[[4-(2,2,2-trifluoro-1-methylethoxy)-2-pyrimidyl]oxy]-phenylacetate and 2-(methoxyimino)-N-methyl-2-[[4-(2,2,2-trifluoro-1-methylethoxy)-2-pyrimidyl]oxy]-phenylacetamide, which are constitutionally similar prior-art compounds of the same direction of action.

If appropriate, the compounds according to the invention can be present as mixtures of different possible isomeric forms, in particular of stereoisomers, such as, for example, E- and Z, or optical isomers. What is claimed are both the E and the Z isomers, the individual enantiomers, the racemates, and any mixtures of these isomers.

Preference is given to pyrimidyloxyphenylacetic acid derivatives of the formula (I) in which R represents alkyl having 4 to 12 carbon atoms which is optionally mono- to n-substituted (where n represents the number of the hydrogen atoms of the unsubstituted hydrocarbon radical in question) by halogen and/or 1 to 2 alkoxy groups having 1 to 8 carbon atoms, Q represents oxygen or —NH— and $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, and preferably represents hydrogen or methyl and in particular hydrogen.

Preference is also given to pyrimidyloxyphenylacetic acid derivatives of the formula (I) in which R represents methyl which is optionally mono-, di- or trisubstituted by halogen or represents ethyl which is optionally mono-, di-, tetra- or penta-substituted by halogen and/or 1 to 2 alkoxy groups having 1 to 8 carbon atoms, or represents n-propyl which is optionally mono-, di-, tri-, tetra- penta-, hexa- or hepta-substituted by halogen and/or 1 to 2 alkoxy groups having 1 to 8 carbon atoms or represents i-propyl which is optionally mono-, di-, tetra-, penta-, hexa- or hepta-substituted by halogen and/or 1 to 2 alkoxy groups having 1 to 8 carbon atoms, Q represents oxygen or —NH— and $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular hydrogen.

Preference is furthermore given to pyrimidyloxyphenylacetic acid derivatives of the formula (I) in which R represents alkenyl or alkinyl having 2 to 12 carbon atoms which is optionally mono- to n-substituted (where n is the number of the hydrogen atoms of the unsubstituted hydrocarbon radical in question) by halogen and/or 1 to 2 alkoxy groups having 1 to 8 carbon atoms and/or 1 to 2 cycloalkyl groups having 3 to 6 carbon atoms (which for their part may optionally be substituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms), Q represents oxygen or —NH— and $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular hydrogen.

Preference is furthermore given to pyrimidyloxyphenylacetic acid derivatives of the formula (I) in which R represents cycloalkyl, cycloalkenyl, cycloalkylalkyl or cycloalkenylalkyl having 3 to 8 carbon atoms in the cycloalkyl or cycloalkenyl moiety and 1 to 4 carbon atoms in the alkyl moiety, which is optionally mono- to pentasubstituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms, Q represents oxygen or —NH— and $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular hydrogen.

Particular preference is given to pyrimidyloxyphenylacetic acid derivatives of the formula (I) in which R represents n-, i-, s- or t-butyl, 1-, 2-, 3-, neo-pentyl, 1-, 2-, 3-, 4-(2-methylbutyl),1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl, n-heptyl-, n-octyl-, n-nonyl-, n-decyl, n-undecyl, n-dodecyl, which is optionally mono- to n-substituted (where n is the number of the hydrogen atoms of the unsubstituted hydrocarbon radical in question) by fluorine, chlorine or bromine and/or mono- to disubstituted by methoxy or ethoxy, Q represents oxygen or —NH— and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular hydrogen.

Particular preference is also given to pyrimidyloxyphenylacetic acid derivatives of the formula (I) in which R represents methyl which is optionally mono-, di- or trisubstituted by fluorine, chlorine or bromine or ethyl which is optionally mono-, di-, tetra- or penta-substituted by fluorine, chlorine, bromine and/or mono- to disubstituted by methoxy or ethoxy, or represents n-propyl which is optionally mono-, di-, tri-, tetra-, penta-, hexa- or hepta-substituted by fluorine, chlorine, bromine and/or mono- to disubstituted by methoxy or ethoxy or represents i-propyl which is optionally mono-, di-, tetra-, penta-, hexa- or hepta-substituted by fluorine, chlorine, bromine and/or mono- to disubstituted by methoxy or ethoxy, Q represents oxygen or —NH— and L¹, L², L³ and L⁴ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular hydrogen.

Particular preference is furthermore given to pyrimidyloxyphenylacetic acid derivatives of the formula (I) in which R represents optionally mono- to n-substituted allyl, but-2-ene-1-yl, propargyl or but-2-in-1-yl, suitable substituents preferably being the atoms and groups mentioned below: in each case 1 to n (where n is the number of the hydrogen atoms of the unsubstituted hydrocarbon radical in question) fluorine, chlorine or bromine atoms, in each case 1 to 2 methoxy or ethoxy groups and/or in each case 1 to 2 cyclopropyl, cyclobutyl, cyclopentyl or cyclohexyl groups, where the cycloalkyl groups are in each case optionally mono- to pentasubstituted by fluorine, chlorine, methyl or ethyl, Q represents oxygen or —NH— and L¹, L², L³ and L⁴ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular hydrogen.

Particular preference is furthermore given to pyrimidyloxyphenylacetic acid derivatives of the formula (I) in which R represents cyclopropyl, cyclobutyl, cyclopentyl, cyclohexyl, cycloheptyl, cyclopropylmethyl, cyclobutylmethyl, cyclopentylmethyl, cyclohexylmethyl or cycloheptylmethyl cyclopropenyl, cyclobutenyl, cyclopentenyl, cyclohexenyl, cycloheptenyl, cyclopropenylmethyl, cyclobutenylmethyl, cyclopentenylmethyl, cyclohexenylmethyl or cycloheptenylmethyl which is optionally mono-, di-, tri-, tetra- or pentasubstituted by fluorine, chlorine, bromine, methyl, ethyl, vinyl, allyl, trifluoromethyl, dimethylvinyl or dichlorovinyl, Q represents oxygen or —NH— and L¹, L², L³ and L⁴ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular hydrogen.

The abovementioned general or preferred radical definitions apply both to the end products of the formula (I) and, correspondingly, to the starting materials or intermediates required in each case for the preparation.

The radical definitions given specifically for these radicals in the respective combinations or preferred combinations of radicals are, independently of the combination given in each case, also replaced as desired by radical definitions of other preferred ranges.

The formula (II) provides a general definition of the 4-halogeno-2-phenoxypyrimidines required as starting materials for carrying out the process a) according to the invention. In this formula (II), Q, L¹, L², L³ and L⁴ preferably or in particular have those meanings which have already been mentioned in connection with the description of the compounds of the formula (I) according to the invention as being preferred or as being particularly preferred for Q, L¹, L², L³ and L⁴. X represents halogen, preferably chlorine.

The 4-halogeno-2-phenoxypyrimidines of the formula (II) have hitherto not been known, as novel substances, they also form part of the subject matter of the present application.

They are obtained (process c) when 4-halogeno-2-alkylsulfonylpyrimidines of the general formula (VI)

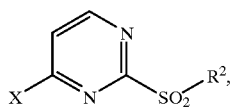

(VI)

in which

X is as defined above and

R² represents alkyl or arylalkyl are reacted with a 2-(1-hydroxyphenyl-1-methoximino) acetic acid derivative of the general formula (V), if appropriate in the presence of a diluent and if appropriate in the presence of an acid acceptor.

The formula (VI) provides a general definition of the 4-halogeno-2-alkylsulphonylpyrimidines required as starting materials for carrying out the process c) according to the invention. In this formula (VI), X preferably or in particular has that meaning which has already been mentioned in connection with the description of the intermediates of the formula (II) according to the invention as being preferred or as being particularly preferred for X. R² represents alkyl or arylalkyl, preferably methyl or benzyl.

The 4-halogeno-2-alkylsulphonylpyrimidines of the formula (VI) are known and can be prepared by known processes (compare, for example, heterocycles (1985), 23(3), 611–16).

The formula (V) provides a general definition of the 2-(1-hydroxyphenyl-1-methoximino)acetic acid derivatives furthermore required as starting materials for carrying out the process (c) according to the invention. In this formula (V), Q, L¹, L², L³ and L⁴ preferably or in particular have those meanings which have already been mentioned in connection with the description of the compounds of the formula (I) according to the invention as being preferred or as being particularly preferred for Q, L¹, L², L³ and L⁴.

The 2-(1-hydroxyphenyl-1-methoximino)acetic acid derivatives of the formula (V) are known and can be prepared by known processes (compare, for example, WO 95-24396 or GB 2249092).

The formula (III) provides a general definition of the alcohols furthermore required as starting materials for carrying out the process a) according to the invention. In this formula (III), R preferably or in particular has those meanings which have already been mentioned in connection with the description of the compounds of the formula (I) according to the invention as being preferred or as being particularly preferred for R.

The alcohols of the formula (III) are known chemicals for synthesis.

The formula (IV) provides a general definition of the alkylsulphonylpyrimidines required as starting materials for carrying out the process b) according to the invention. In this formula (IV), R preferably or in particular has that meaning which has already been mentioned in connection with the description of the compounds of the formula (I) according to the invention as being preferred or as being particularly preferred for R. $R^1$ represents alkyl or arylalkyl, preferably methyl or benzyl.

The alkylsulphonylpyrimidines of the formula (IV) are known and can be prepared by known processes (compare, for example, WO 95-24396 or Chem. Ber., 101, 1968, 2132).

The 3-(1-hydroxyphenyl-1-alkoximinomethyl)dioxazines furthermore required as starting materials for carrying out the process b) according to the invention have already been described above, under the description of the process c) according to the invention.

Suitable diluents for carrying out the processes a), b) and c) according to the invention are all inert organic solvents. These preferably include ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulphoxides, such as dimethyl sulphoxide; or sulphones, such as sulpholane.

The processes a), b) and c) according to the invention are, if appropriate, carried out in the presence of a suitable acid acceptor. Suitable acid acceptors are all customary inorganic or organic bases. These preferably include alkaline earth metal or alkali metal hydrides, amides, hydroxides, alkoxides, carbonates, bicarbonates, and also alkaline earth metal or alkali metal alkyl compounds, such as, for example, sodium hydride, sodium amide, sodium tert-butoxide, sodium hydroxide, potassium hydroxide, potassium carbonate, potassium carbonate, potassium bicarbonate, sodium bicarbonate or butyllitium.

When carrying out the processes a), b) and c) according to the invention, the reaction temperatures can be varied within a relatively wide range. In general, the processes are carried out at temperatures from –20° C. to 130° C., preferably at temperatures from –10° C. to 80° C.

For carrying out the process a) according to the invention for preparing the compounds of the formula (I), generally 0.5 to 5 mol, preferably 0.8 to 2 mol, of an alcohol of the formula (III) are employed per mole of 4-halogeno-2-phenoxypyrimidine of the formula (II).

For carrying out the process b) according to the invention for preparing the compounds of the formula (I), generally 0.5 to 5 mol, preferably 0.8 to 2 mol, of a 2-(1-hydroxyphenyl-1-methoximino)acetic acid derivative of the formula (V) are employed per mole of alkylsulphonylpyrimidine of the formula (IV).

For carrying out process c) according to the invention for preparing the compounds of the formula (II), generally 0.5 to 5 mol, preferably 0.8 to 2 mol, of a 2-(1-hydroxyphenyl-1-methoximino)acetic acid derivative of the formula (V) are employed per mole of 4-halogeno-2-alkylsulphonylpyrimidine of the formula (VI).

The processes according to the invention are generally carried out under atmospheric pressure. However, it is also possible to operate under elevated or reduced pressure—generally between 0.1 bar and 10 bar.

The practice of the reaction and the work-up and isolation of the reaction products are carried out by generally customary processes (compare also the Preparation Examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, Leptosphaeria- or Pyrenophora-species, diseases in viticulture and fruit and vegetable growing, such as, for example, against Venturia, Podosphaera and Phytophtora species. rice diseases, such as, for example, Pyricularia species, are also controlled very successfully.

The active compounds according to the invention may also be employed to increase the yield of crops. Moreover, they have low toxicity and are tolerated well by plants.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ for example organic solvents as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacrilisobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfosufen (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozcene(PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole- 1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro [4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl[(4-chlorophenyl)-azo]-cyanoacetate, potassium hydrogen carbonate, methanetetrathiol sodium salt, methyl1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulfonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-mono-sodium salt, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, diinethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compounds are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

Preparation Examples

EXAMPLE (1)

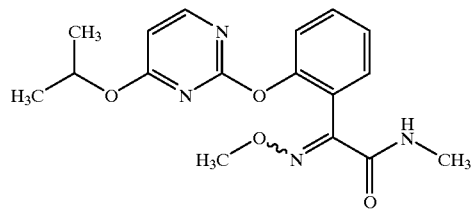

Process b)

0.2 g (0.005 mol) of an 80% strength suspension of sodium hydride is added to a solution of 1.1 g (0.005 mol) of 4-isopropoxy-2-methylsulphonylpyrimidine and 1.0 g (0.005 mol) of 2-(2-hydroxyphenyl)-2-methoxyimino-N-methylacetamide in 20 ml of dimethylformamide, and the mixture is stirred at room temperature for 48 hours. The mixture is taken up in ethyl acetate, washed twice with water, dried over sodium sulphate and concentrated under reduced pressure. This gives 1.4 g (65% of theory) of 2-[2-(4-isopropoxypyrimidin-2-yloxy)-phenyl]-2-methoxyimino-N-methylacetamide. HPLC: logP=2.20

The logP values were determined in accordance with EEC directive 79/831 Annex V. A8 by HPLC (gradient method, acetonitrile/0.1% aqueous phosphoric acid)

Analogously to Example (1), and according to the general description of the preparation processes a) and b) according to the invention, the compounds of the formula (I-a) according to the invention listed in Table 1 below are likewise obtained:

TABLE 1

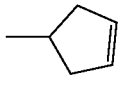
(I-a)

| Example | Q | R | logP | melting point (° C.) |
|---|---|---|---|---|
| 2 | O | —CH₃ | | |
| 3 | O | —C₂H₅ | 2.5 | |
| 4 | O | n-propyl | | |
| 5 | O | i-propyl | | |
| 6 | O | n-butyl | | |
| 7 | O | i-butyl | | |
| 8 | O | 2-butyl | | |
| 9 | O | t-butyl | | |
| 10 | O | n-pentyl | | |
| 11 | O | 3-methylbutyl | | |
| 12 | O | n-hexyl | | |
| 13 | O | cyclopropyl | | |
| 14 | O | Cyclobutyl | | |
| 15 | O | cyclopentyl | | |
| 16 | O | cyclohexyl | | |
| 17 | O | cycloheptyl | | |
| 18 | O | 2-methylcyclopentyl | | |
| 19 | O | 2-methylcyclohexyl | | |
| 20 | O | 3-methylcyclohexyl | | |
| 21 | O | 4-methylcyclohexyl | | |
| 22 | O | cyclopropylmethyl | | |
| 23 | O | cyclobutylmethyl | | |
| 24 | O | cyclopentylmethyl | | |
| 25 | O | cyclohexylmethyl | | |
| 26 | O | allyl | | |
| 27 | O | but-2-en-1-yl | | |
| 28 | O | 3-methyl-but-2-en-1-yl | | |
| 29 | O | 2-methylallyl | | |
| 30 | O | 2,3-dimethyl-but-2-en-1-yl | | |
| 31 | O | 3,3-dichloroallyl | | |
| 32 | O | 2,3,3-trichloroallyl | | |
| 33 | O | 2-chloroallyl | | |
| 34 | O | 2-(chloromethyl-allyl | | |
| 35 | O | propargyl | | |
| 36 | O | but-2-in-1-yl | | |
| 37 | O | pent-2-in-1-yl | | |
| 38 | O | 5-fluoropent-2-in-1-yl | | |
| 39 | O | 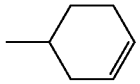 | | |
| 40 | O | 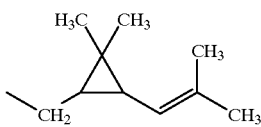 | | |
| 41 | O | 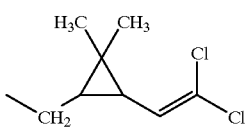 | | |
| 42 | O | 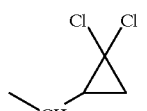 | | |

TABLE 1-continued

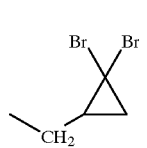
(I-a)

| Example | Q | R | logP | melting point (° C.) |
|---|---|---|---|---|
| 43 | O | 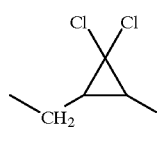 | | |
| 44 | O | 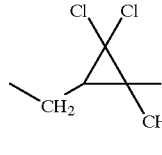 | | |
| 45 | O | 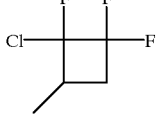 | | |
| 46 | O | 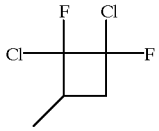 | | |
| 47 | O | 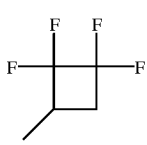 | | |
| 48 | O | 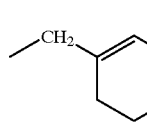 | | |
| 49 | O | 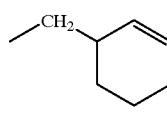 | | |
| 50 | O |  | | |
| 51 | O |  | | |

TABLE 1-continued

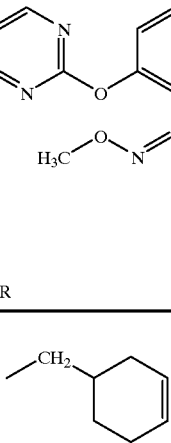

(I-a)

| Example | Q | R | logP | melting point (° C.) |
|---|---|---|---|---|
| 52 | O | 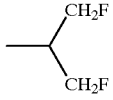 | | |
| 53 | O | —CH₂—CH₂—Cl | | |
| 54 | O | —CH₂—CHCl₂ | | |
| 55 | O | —CH₂—CCl₃ | | |
| 56 | O | —CH₂—CH₂—F | | |
| 57 | O | —CH₂—CBr₃ | | |
| 58 | O | —CH₂—CH₂—CH₂—Cl | | |
| 59 | O | —CH₂—CH(Cl)—CH₂Cl | | |
| 60 | O | —CH₂—CH(Br)—CH₂—Br | | |
| 61 | O | —CH₂—CH₂—CH₂—Br | | |
| 62 | O | —CH₂—CH₂—CF₃ | | |
| 63 | O | —CF₂—CH₂—CHF₂ | | |
| 64 | O | —CH₂—CF₂—CF₃ | 3.35 | |
| 65 | O | 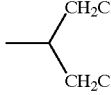 | | |
| 66 | O | 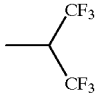 | | |
| 67 | O | 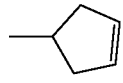 | | |
| 68 | O | —CH₃ | | |
| 69 | O | —C₂H₅ | | |
| 70 | O | n-propyl | | |
| 71 | O | n-butyl | 2.6 | |
| 72 | O | i-butyl | | |
| 73 | NH | 2-butyl | | |
| 74 | NH | t-butyl | | |
| 75 | NH | n-pentyl | | |
| 76 | NH | 3-methylbutyl | | |
| 77 | NH | n-hexyl | | |
| 78 | NH | cyclopropyl | | |
| 79 | NH | cyclobutyl | | |
| 80 | NH | cyclopentyl | 2.6 | |
| 81 | NH | cyclohexyl | | |
| 82 | NH | cycloheptyl | | |
| 83 | NH | 2-methylcyclopentyl | | |
| 84 | NH | 2-methylcyclohexyl | | |
| 85 | NH | 3-methylcyclohexyl | | |
| 86 | NH | 4-methylcyclohexyl | | |
| 87 | NH | cyclopropylmethyl | 2.2 | |
| 88 | NH | cyclobutylmethyl | | |
| 89 | NH | cyclopentylmethyl | | |
| 90 | NH | cyclohexylmethyl | | |
| 91 | NH | allyl | | |

TABLE 1-continued

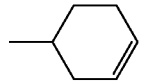

(I-a)

| Example | Q | R | logP | melting point (° C.) |
|---|---|---|---|---|
| 92 | NH | but-2-en-1-yl | | |
| 93 | NH | 3-methyl-but-2-en-1-yl | | |
| 94 | NH | 2-methylallyl | | |
| 95 | NH | 2,3-dimethyl-but-2-en-1-yl | | |
| 96 | NH | 3,3-dichloroallyl | | |
| 97 | NH | 2,3,3-trichloroallyl | | |
| 98 | NH | 2-chloroallyl | | |
| 99 | NH | 2-(chloromethyl-allyl | | |
| 100 | NH | propargyl | | |
| 101 | NH | but-2-in-1-yl | | |
| 102 | NH | pent-2-in-1-yl | | |
| 103 | NH | 5-fluoropent-2-in-1-yl | | |
| 104 | NH | 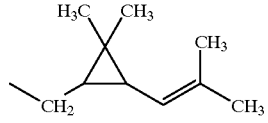 | | |
| 105 | NH | 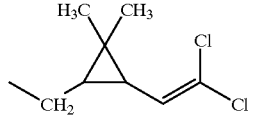 | | |
| 106 | NH | 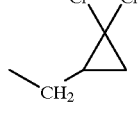 | | |
| 107 | NH | 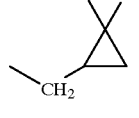 | | |
| 108 | NH | 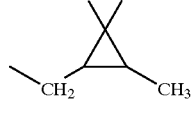 | | |
| 109 | NH |  | | |
| 110 | NH |  | | |

TABLE 1-continued

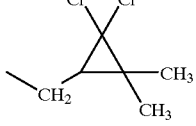

(I-a)

| Example | Q | R | logP | melting point (° C.) |
|---|---|---|---|---|
| 111 | NH | 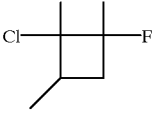 | | |
| 112 | NH | 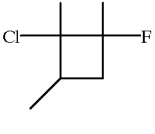 | | |
| 113 | NH | 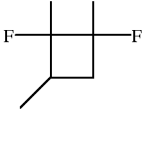 | | |
| 114 | NH | 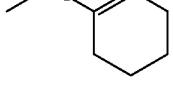 | | |
| 115 | NH | 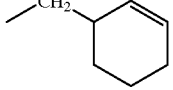 | | |
| 116 | NH | 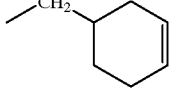 | | |
| 117 | NH | 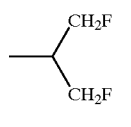 | | |
| 118 | NH | —CH₂—CH₂—Cl | | |
| 119 | NH | —CH₂—CHCl₂ | | |
| 120 | NH | —CH₂—CCl₃ | | |
| 121 | NH | —CH₂—CH₂—F | | 122 |
| 122 | NH | —CH₂—CBr₃ | | |
| 123 | NH | —CH₂—CH₂—CH₂—Cl | | |
| 124 | NH | —CH₂—CH(Cl)—CH₂Cl | | |
| 125 | NH | —CH₂—CH(Br)—CH₂—Br | | |
| 126 | NH | —CH₂—CH₂—CH₂—Br | 2.3 | |
| 127 | NH | —CH₂—CH₂—CF₃ | | |
| 128 | NH | —CF₂—CH₂—CHF₂ | | |
| 129 | NH | —CH₂—CF₂—CF₃ | 2.8 | |
| 130 | NH | 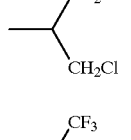 | 2.0 | |
| 131 | NH | 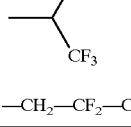 | | |
| 132 | NH | (CF₃)₂CH— | 3.1 | 122 |
| 133 | NH | —CH₂—CF₂—CHF₂ | 2.4 | |

Use Examples

Example A

Erysiphe test (wheat)/curative
Solvent: 25 parts by weight of N,N-dimethylacetamide
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. tritici. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew postules.

The valuation is carried out 7 days after the inoculation. 0% means an efficacy which corresponds to that of the control, whereas an efficacy of 100% means that no infection is observed.

In this test, for example, the compounds of Preparation Examples (3) and (129) exhibit, at an exemplary active compound application rate of 125 g/ha, an efficacy of 100% in comparison to the untreated control.

Example B

Erysiphe test (barley)/protective
Solvent: 25 parts by weight of N,N-dimethylacetamide
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. hordei.

The plants are placed in a greenhouse at a temperature of approximately 20° C. and a relative atmospheric humidity of approximately 80% to promote the development of mildew postules.

Evaluation is carried out 7 days after the inoculation. 0% means an efficacy which corresponds to that of the control, whereas an efficacy of 100% means that no infection is observed.

In this test, for example, the compounds of Preparation Examples (3) and (129) exhibit, at an exemplary active compound application rate of 125 g/ha, an efficacy of 100% in comparison to the untreated control.

Example C

Leptosphaeria nodorum test (wheat)/curative
  Solvent: 10 parts by weight of N-methyl-pyrrolidone
  Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Leptosphaeria nodorum. The plants remain in an incubation cabin at 20° C. and 100% relative atmospheric humidity for 48 hours and are then sprayed with the preparation of active compound at the stated application rate.

The plants are placed in a greenhouse at a temperature of approximately 15° C. and a relative atmospheric humidity of approximately 80%.

Evaluation is carried out 10 days after the inoculation. 0% means an efficacy which corresponds to that of the control, whereas an efficacy of 100% means that no infection is observed.

In this test, for example, the compound of Preparation Example (1) exhibits, at an exemplary active compound application rate of 125 g/ha, an efficacy of more than 60% in comparison to the untreated control. In contrast, the known compounds methyl 2-(methoxyimino)-2-[[4-(2,2,2-trifluoroethoxy)-2-pyrimidyl]oxy]-phenylacetate, 2-(methoxyimino)-N-methyl-2-[[4-(2,2,2-tri fluoroethoxy)-2-pyrimidyl]oxy]-phenylacetamide, 2-(methoxyimino)-N-methyl-2-[[4-(2,2,2-trifluoro-1-methylethoxy)-2-pyrimidyl]oxy]-phenylacetamide achieve, under the same conditions, only efficacies between 0% and 18%.

Example D

Pyrenophora teres test (barley)/curative
  Solvent: 10 parts by weight of N-methyl-pyrrolidone
  Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Pyrenophora teres. The plants remain in an incubation cabin at 20° C. and 100% relative atmospheric humidity for 48 hours. The plants are subsequently sprayed with the preparation of active compound at the stated application rate.

The plants are placed in a greenhouse at a temperature of approximately 20° C. and a relative atmospheric humidity of approximately 80%.

Evaluation is carried out 7 days after the inoculation. 0% means an efficacy which corresponds to that of the control, whereas an efficacy of 100% means that no infection is observed.

In this test, for example, the compound of Preparation Example (1) exhibits, at an exemplary active compound application rate of 250 g/ha, an efficacy of 70% in comparison to the untreated control. In contrast, the known compounds methyl 2-(methoxyimino)-2-[[4-(2,2,2-trifluoroethoxy)-2-pyrimidyl]oxy]-phenylacetate, 2-(methoxyimino)-N-methyl-2-[[4-(2,2,2-trifluoroethoxy)-2-pyrimidyl]oxy]-phenylacetamide, methyl 2-(methoxyimino)-2-[[4-2,2,2-trifluoro-1-methylethoxy)-2-pyrimidyl]oxy]-phenylacetate and 2-(methoxyimino)-N-methyl-2-[[4-(2,2,2-trifluoro-1-methylethoxy)-2-pyrimidyl]oxy]-phenylacetamide achieve, under the same conditions, only efficacies between 16% and 25%.

Example E

Phytophthora test (tomato)/protective
  Solvent: 47 parts by weight of acetone
  Emulsifier: 3 parts by weight of alkylaryl polyglycol ether To produce a suitable preparation of active compound, 1 part by weight of active compound is mixed with stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

In this test, for example, the compounds of Preparation Examples (3) and (129) exhibit, at an exemplary active compound application rate of 100 g/ha, an efficacy of at least 75% in comparison to the untreated control. In contrast, the known compounds methyl 2-(methoxyimino)-2-[[4-(2,2,2-trifluoroethoxy)-2-pyrimidyl]oxy]-phenylacetate and 2-(methoxyimino)-N-methyl-2-[[4-(2,2,2-trifluoro-1-methylethoxy)-2-pyrimidyl]oxy]-phenylacetamide achieve, under the same conditions, only efficacies of below 70%.

Example F

Podosphaera test (apple)/protective
  Solvent: 47 parts by weight of acetone
  Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the compound of Preparation Example (3) exhibits, at an exemplary active compound application rate of 10 g/ha, an efficacy of at least 80% in comparison to the untreated control. In contrast, the known compounds methyl 2-(methoxyimino)-2-[[4-(2,2,2-trifluoroethoxy)-2-pyrimidyl]oxy]-phenyl acetate, 2-(methoxyimino)-N-methyl-2-[[4-(2,2,2-trifluoroethoxy)-2-pyrimidyl]oxy]-phenyl-acetamide, methyl 2-(methoxyimino)-2-[[4-(2,2,2-trifluoro-1-methylethoxy)-2-pyrimidyl]oxy]-phenylacetate and 2-(methoxyimino)-N-methyl-2-[[4-(2,2,2-trifluoro-1-methylethoxy)-2-pyrimidyl]oxy]-phenylacetamide achieve, under the same conditions, only efficacies between 0 and 55%.

Example G

Venturia test (apple)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, for example, the compounds of Preparation Examples (3) and (129) exhibit, at an exemplary active compound application rate of 10 g/ha, an efficacy of more than 90% in comparison to the untreated control. In contrast, the known compounds 2-(methoxyimino)-N-methyl-2-[[4-(2,2,2-trifluoroethoxy)-2-pyrimidyl]oxy]-phenylacetamide and 2-(methoxyimino)-N-methyl-2-[[4-(2,2,2-trifluoro-1-methylethoxy)-2-pyrimidyl]oxy]-phenylacetamide achieve, under the same conditions, only efficacies of below 80%.

We claim:

1. A pyrimidyloxyphenylacetic acid compound of the formula (I)

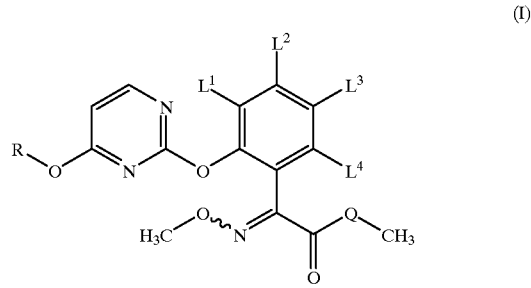

wherein

R is a moiety selected from the group consisting of
unsubstituted alkyl having 4 to 12 carbon atoms; alkyl which is mono- to n-substituted (where n represents the number of the hydrogen atoms of the unsubstituted hydrocarbon radical in question) by halogen and/or is substituted by one or two alkoxy groups having 1 to 8 carbon atoms;

unsubstituted methyl; methyl which is mono-, di- or trisubstituted by halogen; unsubstituted ethyl; ethyl which is mono-, di-, tetra- or penta-substituted by halogen and/or is substituted by 1 to 2 alkoxy groups having 1 to 8 carbon atoms; unsubstituted n-propyl; n-propyl which is mono-, di-, tri-, tetra- penta-, hexa- or hepta-substituted by halogen and/or is substituted by 1 to 2 alkoxy groups having 1 to 8 carbon atoms; unsubstituted i-propyl; i-propyl which is mono-, di-, tetra-, penta-, hexa- or hepta-substituted by halogen and/or is substituted by 1 to 2 alkoxy groups having 1 to 8 carbon atoms;

unsubstituted alkenyl or alkinyl having 2 to 12 carbon atoms; alkenyl or alkinyl having 2 to 12 carbon atoms which is mono- to n-substituted (where n is the number of the hydrogen atoms of the unsubstituted hydrocarbon radical in question) by halogen and/or is substituted by 1 to 2 alkoxy groups having 1 to 8 carbon atoms and/or 1 to 2 cycloalkyl groups having 3 to 6 carbon atoms, and
wherein said alkoxy and/or said cycloalkyl is unsubstituted or is substituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms; and unsubstituted cycloalkyl, cycloalkenyl, cycloalkylalkyl or cycloalkenylalkyl having 3 to 8 carbon atoms in the cycloalkyl or cycloalkenyl moiety and 1 to 4 carbon atoms in the alkyl moiety; cycloalkyl, cycloalkenyl, cycloalkylalkyl or cycloalkenylalkyl having 3 to 8 carbon atoms in the cycloalkyl or cycloalkenyl moiety and 1 to 4 carbon atoms in the alkyl moiety which is mono- to pentasubstituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms;

Q represents oxygen or —NH—, and $L^1$, $L^2$, $L^3$ and $L^4$ are identical or different and independently of one another each represents a moiety selected from the group consisting of hydrogen; halogen; cyano; nitro; unsubstituted alkyl, alkoxy, alkylthio, alkylsulphinyl or alkylsulphonyl having in each case 1 to 6 carbon atoms; and alkyl, alkoxy, alkylthio, alkylsulphinyl or alkylsulphonyl having in each case 1 to 6 carbon atoms which is substituted by 1 to 5 halogen atoms.

2. The compound of claim 1 in which

R represents n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimetylbutyl), 1-, 2-(2,3-dimethylbutyl, n-heptyl-, n-octyl-, n-nonyl-, n-decyl, n-undecyl, n-dodecyl, which is optionally mono- to n-substituted (where n is the number of the hydrogen atoms of the unsubstituted hydrocarbon radical in question) by fluorine, chlorine or bromine and/or mono- to disubstituted by methoxy or ethoxy, Q represents oxygen or —NH— and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. The compound of claim 1 in which

R represents methyl which is optionally mono-, di- or trisubstituted by fluorine, chlorine or bromine or ethyl which is optionally mono-, di-, tetra- or pentasubstituted by fluorine, chlorine, bromine and/or mono- to disubstituted by methoxy or ethoxy, or represents n-propyl which is optionally mono-, di-, tri-, tetra-, penta-, hexa- or hepta-substituted by fluorine, chlorine, bromine and/or mono- to disubstituted by methoxy or ethoxy or represents i-propyl which is optionally mono-, di-, tetra-, penta-, hexa- or hepta-substituted by fluorine, chlorine, bromine and/or mono- to disubstituted by methoxy or ethoxy, Q represents oxygen or —NH— and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

4. The compound of claim 1 in which

R represents optionally mono- to n-substituted allyl, but-2-ene-1-yl, propargyl or but-2-in-1-yl, suitable substituents preferably being the atoms and groups mentioned below: in each case 1 to n (where n is the number of the hydrogen atoms of the unsubstituted hydrocarbon radical in question) fluorine, chlorine or bromine atoms, in each case 1 to 2 methoxy or ethoxy groups and/or in each case 1 to 2 cyclopropyl, cyclobutyl, cyclopentyl or cyclohexyl groups, where the cycloalkyl groups may be mono- to pentasubstituted by fluorine, chlorine, methyl or ethyl, Q represents oxygen or —NH— and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

5. A compound of the formula (I) according to claim 1 in which

R represents cyclopropyl, cyclobutyl, cyclopentyl, cyclohexyl, cycloheptyl, cyclopropylmethyl, cyclobutylmethyl, cyclopentylmethyl, cyclohexylmethyl or cycloheptylmethyl cyclopropenyl, cyclobutenyl, cyclopentenyl, cyclohexenyl, cycloheptenyl, cyclopropenylmethyl, cyclobutenylmethyl, cyclopentenylmethyl, cyclohexenylmethyl or cycloheptenylmethyl which is optionally mono-, di-, tri-, tetra- or pentasubstituted by fluorine, chlorine, bromine, methyl, ethyl, vinyl, allyl, trifluoromethyl, dimethylvinyl or dichlorovinyl, Q represents oxygen or —NH— and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

6. A microbiocidal composition comprising one or more of the compounds of claim 1 and a member selected from the group consisting of extender, surfactants and mixtures thereof.

7. A method for controlling undesirable microorganisms comprising applying a microibiocidally effective amount of the compound claim 1 to said microorganism and/or its habitat.

8. A process for preparing a microbiocidal composition comprising mixing the compound of claim 1 with a member selected from the group consisting of extenders, surfactants and mixtures thereof.

9. A process for preparing a compound of the formula (I)

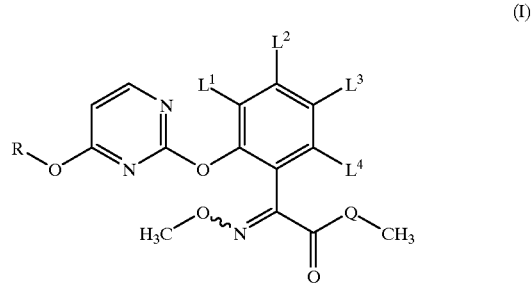

wherein

R is a moiety selected from the group consisting of unsubstituted alkyl having 4 to 12 carbon atoms; alkyl which is mono- to n-substituted (where n represents the number of the hydrogen atoms of the unsubstituted hydrocarbon radical in question) by halogen and/or is substituted by one or two alkoxy groups having 1 to 8 carbon atoms;

unsubstituted methyl; methyl which is mono-, di- or trisubstituted by halogen; unsusbstituted ethyl; ethyl which is mono-, di-, tetra- or penta-substituted by halogen and/or is substituted by 1 to 2 alkoxy groups having 1 to 8 carbon atoms; unsubstituted n-propyl; n-propyl which is mono-, di-, tri-, tetra- penta-, hexa- or hepta-substituted by halogen and/or is substituted by 1 to 2 alkoxy groups having 1 to 8 carbon atoms; unsubstituted i-propyl; i-propyl which is mono-, di-, tetra-, penta-, hexa- or hepta-substituted by halogen and/or is substituted by 1 to 2 alkoxy groups having 1 to 8 carbon atoms;

unsubstituted alkenyl or alkinyl having 2 to 12 carbon atoms; alkenyl or alkinyl having 2 to 12 carbon atoms which is mono- to n-substituted (where n is the number of the hydrogen atoms of the unsubstituted hydrocarbon radical in question) by halogen and/or is substituted by 1 to 2 alkoxy groups having 1 to 8 carbon atoms and/or 1 to 2 cycloalkyl groups having 3 to 6 carbon atoms, and wherein said alkoxy and/or said cycloalkyl is unsubstituted or is substituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms; and unsubstituted cycloalkyl, cycloalkenyl, cycloalkylalkyl or cycloalkenylalkyl having 3 to 8 carbon atoms in the cycloalkyl or cycloalkenyl moiety and 1 to 4 carbon atoms in the alkyl moiety; cycloalkyl, cycloalkenyl, cycloalkylalkyl or cycloalkenylalkyl having 3 to 8 carbon atoms in the cycloalkyl or cycloalkenyl moiety and 1 to 4 carbon atoms in the alkyl moiety which is mono- to pentasubstituted by halogen, alkyl having 1 to 4 carbon atoms, alkenyl having 2 to 4 carbon atoms, halogenoalkyl having 1 to 4 carbon atoms and 1 to 5 halogen atoms or halogenoalkenyl having 2 to 4 carbon atoms and 1 to 3 halogen atoms;

Q represents oxygen or —NH—, and $L^1$, $L^2$, $L^3$ and $L^4$ are identical or different and independently of one another each represents a moiety selected from the group consisting of hydrogen; halogen; cyano; nitro; unsubstituted alkyl, alkoxy, alkylthio, alkylsulphinyl or alkylsulphonyl having in each case 1 to 6 carbon atoms; and alkyl, alkoxy, alkylthio, alkylsulphinyl or alkylsulphonyl having in each case 1 to 6 carbon atoms which is substituted by 1 to 5 halogen atoms;

comprising a) reacting a 4-halogeno-2-phenoxypyrimidines of the formula (II)

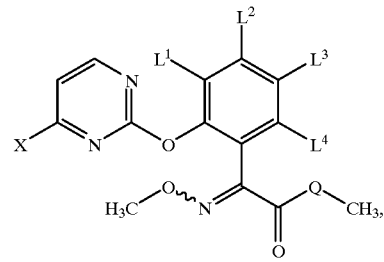

wherein Q, $L^1$, $L^2$, $L^3$ and $L^4$ are as defined above and X represents halogen with an alcohol of the formula

wherein R is as defined above, optionally in the presence of a diluent and optionally in the presence of an acid acceptor, or or b) reacting an alkylsulphonylpyrimidine of the formula (IV)

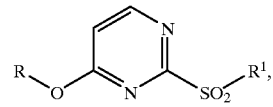

wherein R is as defined above and $R^1$ represents alkyl or arylalkyl with a 2-(1-hydroxyphenyl-1-methoximino)acetic acid derivative of the formula (V)

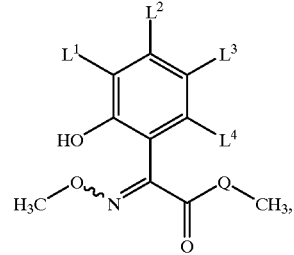

wherein Q, $L^1$, $L^2$, $L^3$ and $L^4$ are as defined above, optionally in the presence of a diluent and optionally in the presence of an acid acceptor.

* * * * *